(12) United States Patent
Dey et al.

(10) Patent No.: US 10,590,112 B2
(45) Date of Patent: Mar. 17, 2020

(54) DIHYDROPYRIMIDINYL BENZAZEPINE CARBOXAMIDE COMPOUNDS

(71) Applicant: Hoffmann-La Roche Inc., Little Falls, NJ (US)

(72) Inventors: Fabian Dey, Basel (CH); Lisha Wang, Basel (CH); Hongying Yun, Shanghai (CN); Weixing Zhang, Shanghai (CN); Zhiwei Zhang, Shanghai (CN); Wei Zhu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/213,308

(22) Filed: Dec. 7, 2018

(65) Prior Publication Data

US 2019/0135788 A1    May 9, 2019

Related U.S. Application Data

(63) Continuation of application No. PCT/EP2017/064107, filed on Jun. 9, 2017.

(51) Int. Cl.

| | |
|---|---|
| *C07D 403/04* | (2006.01) |
| *C07D 471/04* | (2006.01) |
| *A61K 9/48* | (2006.01) |
| *A61K 47/10* | (2017.01) |
| *A61K 9/20* | (2006.01) |
| *A61K 9/28* | (2006.01) |
| *A61K 9/00* | (2006.01) |

(52) U.S. Cl.
CPC .......... *C07D 403/04* (2013.01); *A61K 9/0019* (2013.01); *A61K 9/2018* (2013.01); *A61K 9/2866* (2013.01); *A61K 9/4858* (2013.01); *A61K 47/10* (2013.01); *C07D 471/04* (2013.01)

(58) Field of Classification Search
CPC .... A61K 47/10; A61K 9/0019; A61K 9/2018; A61K 9/2866; A61K 9/4858; C07D 471/04; C07D 403/04
USPC ........................................................ 514/213
See application file for complete search history.

(56) References Cited

U.S. PATENT DOCUMENTS

| | | |
|---|---|---|
| 9,334,268 B2 | 5/2016 | Hoves et al. |
| 9,447,097 B2 | 9/2016 | Hoves et al. |
| 9,475,775 B2 | 10/2016 | Hoves et al. |
| 9,597,333 B2 | 3/2017 | Hoves et al. |
| 9,822,065 B1 | 11/2017 | Hoves et al. |
| 9,890,124 B2 | 2/2018 | Hoves et al. |
| 2003/0187016 A1 | 10/2003 | Crooks et al. |
| 2012/0082658 A1 | 4/2012 | Hershberg et al. |
| 2013/0202629 A1 | 8/2013 | Carson et al. |
| 2016/0257653 A1 | 9/2016 | Hoves et al. |
| 2017/0014423 A1 | 1/2017 | Hoves et al. |
| 2017/0275235 A1 | 9/2017 | Miranda et al. |
| 2018/0134705 A1 | 5/2018 | Cheng et al. |
| 2018/0194735 A1 | 7/2018 | Hoves et al. |
| 2018/0194736 A1 | 7/2018 | Hoves et al. |

FOREIGN PATENT DOCUMENTS

| | | |
|---|---|---|
| CA | 3023154 | 11/2017 |
| EP | 0825186 B1 | 4/2002 |
| WO | 1992/015582 A1 | 9/1992 |
| WO | 2005/076783 A2 | 8/2005 |
| WO | 2007/024612 A2 | 3/2007 |
| WO | 2009/111337 A1 | 9/2009 |
| WO | 2010/054215 A1 | 5/2010 |
| WO | 2010/093436 A2 | 8/2010 |
| WO | 2011/017611 A1 | 2/2011 |
| WO | 2011/022508 A2 | 2/2011 |
| WO | 2011/022509 A2 | 2/2011 |
| WO | 2011/068233 A1 | 6/2011 |
| WO | 2011/139348 A2 | 11/2011 |
| WO | 2012/045090 A2 | 4/2012 |

(Continued)

OTHER PUBLICATIONS (ISR and WO for PCT/EP2017/062058 dated Jun. 22, 2017).
(ISR and WO for PCT/EP2017/062059 dated Jun. 22, 2017).

(Continued)

*Primary Examiner* — Kahsay Habte
(74) *Attorney, Agent, or Firm* — Todd M. Crissey

(57) ABSTRACT

This invention relates to new benzazepine carboxamide compounds of the formula

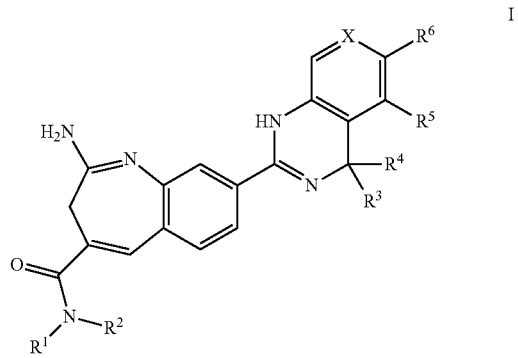

wherein X and $R^1$ to $R^6$ are as defined in the description and in the claims, as well as pharmaceutically acceptable salts thereof. These compounds are TLR8 agonists and may therefore be useful as medicaments for the treatment of diseases such as cancer, autoimmune diseases, inflammation, sepsis, allergy, asthma, graft rejection, graft-versus-host disease, immunodeficiencies, and infectious diseases.

14 Claims, No Drawings

(56) References Cited

FOREIGN PATENT DOCUMENTS

| | | |
|---|---|---|
| WO | 2012/066336 A1 | 5/2012 |
| WO | 2012/097173 A2 | 7/2012 |
| WO | 2012/167081 A1 | 12/2012 |
| WO | 2013/033345 A1 | 3/2013 |
| WO | 2013/067597 A1 | 5/2013 |
| WO | 2013/166110 A1 | 11/2013 |
| WO | 2015/162075 | 10/2015 |
| WO | 2016/096778 | 6/2016 |
| WO | 2016/096778 A1 | 6/2016 |
| WO | 2016/142250 A1 | 9/2016 |
| WO | 2017/046112 | 3/2017 |
| WO | 2017/190669 | 11/2017 |
| WO | 2017/202703 | 11/2017 |
| WO | 2017/202704 | 11/2017 |
| WO | 2017/216054 | 12/2017 |

OTHER PUBLICATIONS (ISR and WO for PCT/EP2017/064107 dated Jul. 21, 2017).
Hennessy et al., "Targeting Toll-Like Receptors: Emerging Therapeutics?" Nature Reviews: Drug Discovery 9:293-307 (Apr 2010).
Holldack, "Toll-Like Receptors as Therapeutic Targets for Cancer" Drug Discovery Today 19(4):379-382 (Apr. 2014).
International Search Report for PCT/EP2015/058465, dated May 26, 2015.
ISR and Written Opinion for PCT/EP2015/079679 (dated Mar. 8, 2016).
ISR for PCT/EP2016/071613 (dated Oct. 31, 2016).
Kawai et al., "The Role of Pattern-Recognition Receptors in Innate Immunity: Update on Toll-Like Receptors" Nature Immunology 11(5):373-384 (May 2010).
Kawai et al., "Toll-Like Receptors and Their Crosstalk with Other Innate Receptors in Infection and Immunity" Immunity 34:637-650 (May 27, 2011).
Uematsu et al., "Toll-Like Receptors and Type I Interferons" Journal of Biological Chemistry 282(21):15319-15323 (May 25, 2007).
Guiducci et al., "RNA recognition by human TLR8 can lead to autoimmune inflammation" The Journal of Experimental Medicine 210(13):2903-2919 (2013).
Smits et al., "The Use of TLR7 and TLR8 Ligands for the Enhancement of Cancer Immunotherapy" The Oncologist 13:859-875 (2008).
(ISR for PCT/EP2016/054487 dated May 3, 2016).
(Written Opinion for PCT/EP2015/058465 dated Oct. 29, 2015).
(Written Opinion for PCT/EP2016/054487 dated Sep. 15, 2016).

DIHYDROPYRIMIDINYL BENZAZEPINE CARBOXAMIDE COMPOUNDS

CROSS-REFERENCE TO RELATED APPLICATIONS

This application is a continuation of International Application No. PCT/EP2017/064107, filed Jun. 9, 2017, claiming priority to Application No. PCT/CN2016/085471 filed Jun. 12, 2016, each of which are incorporated herein by reference in its entirety.

FIELD OF THE INVENTION

The present invention relates to novel dihydropyrimidinyl benzazepine carboxamide compounds having pharmaceutical activity, their manufacture, pharmaceutical compositions containing them and their potential use as medicaments.

In particular, the present invention relates to compounds of the formula

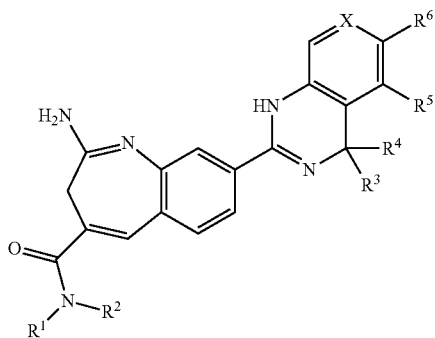

I wherein X and $R^1$ to $R^6$ are as described below, or to pharmaceutically acceptable salts thereof.

The compounds are TLR agonists. More particularly, the compounds are TLR8 agonists and may be useful for the treatment and prevention (e.g. vaccination) of cancer, autoimmune diseases, inflammation, sepsis, allergy, asthma, graft rejection, graft-versus-host disease, immunodeficiencies, and infectious diseases.

Toll-like receptors (TLRs) are a family of membrane-spanning receptors that are expressed on cells of the immune system like dendritic cells, macrophages, monocytes, T cells, B cells, NK cells and mast cells but also on a variety of non-immune cells such as endothelial cells, epithelial cells and even tumor cells (Kawai et al., Immunity, 2011, 34, 637-650, Kawai et al., Nat. Immunol., 2010, 11, 373-384). TLRs that recognize bacterial and fungal components are expressed on the cell surface (i.e. TLR1, 2, 4, 5 and 6), while others that recognize viral or microbial nucleic acids like TLR3, 7, 8 and 9 are localized to the endolysosomal/phagosomal compartment (Henessy et al. Nat. Rev. Drug Discovery 2010, 9, 293-307) and predominantly found to be expressed by cells of the myeloid lineage. TLR ligation leads to activation of NF-κB and IRF-dependent pathways with the specific activation sequence and response with respect to the specific TLR and cell type. While TLR7 is mainly expressed in all dendritic cells subtypes (DC and here highly in pDC, plasmacytoid DC) and can be induced in B cells upon IFNα stimulation (Bekeredjian-Ding et al. J. Immunology 2005, 174:4043-4050), TLR8 expression is rather restricted to monocytes, macrophages and myeloid DC. TLR8 signaling via MyD88 can be activated by bacterial single stranded RNA, small molecule agonists and lately discovered microRNAs (Chen et al. RNA 2013, 19:737-739). The activation of TLR8 results in the production of various pro-inflammatory cytokines such as IL-6, IL-12 and TNF-α as well as enhanced expression of co-stimulatory molecules, such as CD80, CD86, and chemokine receptors (Cros et al. Immunity 2010, 33:375-386). In addition, TLR8 activation can induce type I interferon (IFNβ) in primary human monocytes (Pang et al. BMC Immunology 2011, 12:55).

Small molecule agonists for both the TLR7 and TLR8 receptor as well as analogs modified for use as vaccine adjuvants or conjugates have been identified in many patents (i.e. WO1992015582, WO2007024612, WO2009111337, WO2010093436, WO2011017611, WO2011068233, WO2011139348, WO2012066336, WO2012167081, WO2013033345, WO2013166110, and US2013202629). Clinical experience has been obtained mainly for TLR7 agonists, but only very few clinical studies focused on using highly specific TLR8 agonists. To date, the only FDA (U.S. Food and Drug Administration)-approved small molecule drug is the TLR7 agonist imiquimod (ALDARA™) as a topical agent for the treatment of genital warts, superficial basal cell carcinoma and actinic keratosis. Systemic application however of the early TLR7 agonists like resiquimod has been abandoned due to intolerable cardiotoxicity observed upon global chemokine stimulation at therapeutic levels (Holldack, Drug Discovery Today, 2013, 1-4). Knowledge about TLR8 agonists is less advanced and mostly restricted to data with early mixed TLR7/8 agonists like resiquimod. For the resiquimod agonist, however, the stimulatory capacity of the TLR7 is superior compared to the activation of the TLR8, so that most of the effects of resiquimod are dominated by the effect of TLR7 activity. More recently, TLR8 specific compounds like VTX-2337 have been described by VentiRX Pharmaceuticals (i.e. WO 2007024612), allowing for the first time to analyse the specific role of TLR8 without activation of TLR7 at the same time. At present there is still a need for small molecule TLR8 agonists, specifically those with improved potency or selectivity.

The present invention is directed to benzazepine compounds with improved cellular potency over known TLR8 agonists of this type for use in the treatment of cancer, preferably solid tumors and lymphomas, and for other uses including the treatment of certain skin conditions or diseases, such as atopic dermatitis, the treatment of infectious diseases, preferably viral diseases, and for use as adjuvants in vaccines formulated for use in cancer therapy or by desensitizing of the receptors by continuous stimulation in the treatment of autoimmune diseases.

The new compounds are characterized by improved cellular potency at TLR8 compared to known TLR8 agonists such as VTX-2337. In addition, these compounds are highly specific towards TLR8 and possess only low or even no activity towards TLR7. Due to the more restricted expression pattern of TLR8 less severe side effects when administered systemically are expected and thus the compounds possess advantageous properties compared to combined TLR7/8 agonists.

SUMMARY OF THE INVENTION

The present invention relates to benzazepine-4-carboxamide compounds of the formula

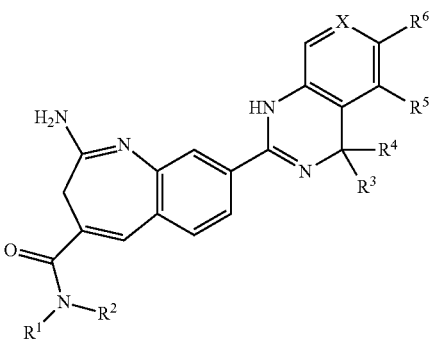

I wherein
R¹ is C$_{3-7}$-alkyl;
R² is C$_{3-7}$-alkyl or C$_{3-7}$-cycloalkyl-C$_{1-7}$-alkyl;
R³ is hydrogen or C$_{1-7}$-alkyl;
R⁴ is hydrogen or C$_{1-7}$-alkyl;
R⁵ is selected from the group consisting of hydrogen, halogen, C$_{1-7}$-alkyl and C$_{1-7}$-alkoxy;
R⁶ is selected from the group consisting of hydrogen, halogen, C$_{1-7}$-alkyl and C$_{1-7}$-alkoxy;
X is N or CR⁷, wherein R⁷ is selected from the group consisting of hydrogen, halogen, C$_{1-7}$-alkyl and C$_{1-7}$-alkoxy;
or pharmaceutically acceptable salts thereof.

The invention is also concerned with processes for the manufacture of compounds of formula I.

The invention also relates to pharmaceutical compositions comprising a compound of formula I as described above and a pharmaceutically acceptable carrier and/or adjuvant.

A further aspect of the invention is the use of compounds of formula I as therapeutic active substances for the treatment of diseases that can be mediated with TLR agonists, in particular TLR8 agonists. The invention thus also relates to a method for the treatment of a disease that can be mediated with TLR agonists such as for example cancer and autoimmune or infectious diseases.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

The nomenclature used in this application is based on IUPAC systematic nomenclature, unless indicated otherwise.

The term "compound(s) of this invention" and "compound(s) of the present invention" refers to compounds of formula I and solvates or salts thereof (e.g., pharmaceutically acceptable salts).

The term "substituent" denotes an atom or a group of atoms replacing a hydrogen atom on the parent molecule.

The term "lower alkyl" or "C$_{1-7}$-alkyl", alone or in combination, signifies a straight-chain or branched-chain optionally substituted alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched C$_{1-7}$-alkyl groups are methyl, ethyl, n-propyl, isopropyl, n-butyl, isobutyl, tert-butyl, the isomeric pentyls, the isomeric hexyls and the isomeric heptyls. Methyl, ethyl, n-propyl, isopropyl, n-butyl, isobutyl and tert-butyl are particularly preferred.

The term "C$_{3-7}$-alkyl" likewise refers to a straight-chain or branched-chain alkyl group with 3 to 7 carbon atoms as defined above. n-propyl is particularly preferred.

The term "C$_{3-7}$-cycloalkyl-C$_{1-7}$-alkyl" refers to lower alkyl groups as defined above wherein at least one of the hydrogen atoms of the lower alkyl group is replaced by a cycloalkyl group. Among the cycloalkylalkyl groups of particular interest is cyclopropylmethyl.

The term "cycloalkyl" or "C$_{3-7}$-cycloalkyl" denotes a saturated carbocyclic group containing from 3 to 7 carbon atoms, such as cyclopropyl, cyclobutyl, cyclopentyl, cyclohexyl or cycloheptyl, more particularly cyclopropyl.

The term "C$_{3-7}$-cycloalkyl-C$_{1-7}$-alkyl" refers to lower alkyl groups as defined above wherein at least one of the hydrogen atoms of the lower alkyl group is replaced by a cycloalkyl group. Among the lower cycloalkylalkyl groups of particular interest is cyclopropylmethyl.

The term "halogen" refers to fluoro, chloro, bromo and iodo, with fluoro, chloro and bromo being of particular interest. More particularly, halogen refers to fluoro or chloro.

The term "lower alkoxy" or "C$_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert-butoxy, in particular methoxy.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Pharmaceutically acceptable salts include both acid and base addition salts. The salts are for example acid addition salts of compounds of formula I with physiologically compatible mineral acids, such as hydrochloric acid, hydrobromic acid, nitric acid, carbonic acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, embonic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium, zinc, copper, manganese and aluminium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, histidine, caffeine, procaine, hydrabamine, choline, betaine, ethylendiamine, glucosamine, methylglucamine, theobromine, piperazine, N-ethylpiperidine, piperidine and polyamine resins. The compound of formula I can also be present in the form of zwitterions. Pharmaceutically acceptable salts of compounds of formula I of particular interest are the sodium salts or salts with tertiary amines.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "half maximal effective concentration" ($EC_{50}$) denotes the plasma concentration of a particular compound required for obtaining 50% of the maximum of a particular effect in vivo.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgment of the attending medical or veterinary practitioner, and other factors.

In detail, the present invention relates to compounds of the formula

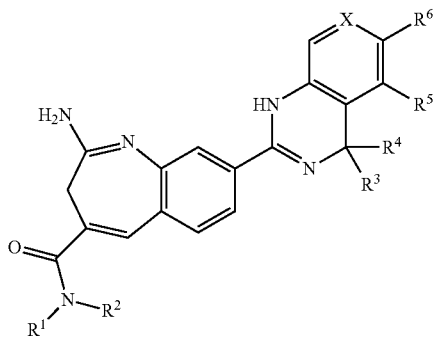

I wherein
$R^1$ is $C_{3-7}$-alkyl;
$R^2$ is $C_{3-7}$-alkyl or $C_{3-7}$-cycloalkyl-$C_{1-7}$-alkyl;
$R^3$ is hydrogen or $C_{1-7}$-alkyl;
$R^4$ is hydrogen or $C_{1-7}$-alkyl;
$R^5$ is selected from the group consisting of hydrogen, halogen, $C_{1-7}$-alkyl and $C_{1-7}$-alkoxy;

$R^6$ is selected from the group consisting of hydrogen, halogen, $C_{1-7}$-alkyl and $C_{1-7}$-alkoxy;
X is N or $CR^7$, wherein $R^7$ is selected from the group consisting of hydrogen, halogen, $C_{1-7}$-alkyl and $C_{1-7}$-alkoxy;
or pharmaceutically acceptable salts thereof.

In a particular aspect, the invention relates to compounds of formula I, wherein $R^1$ is n-propyl.

In another aspect, provided are compounds of formula I, wherein $R^2$ is selected from the group consisting of n-propyl, isobutyl and cyclopropylmethyl. In particular, the invention is concerned with compounds of formula I, wherein $R^1$ and $R^2$ are n-propyl.

In a further aspect, the invention relates to compounds of formula I as defined herein before, wherein $R^3$ is hydrogen or $C_{1-7}$-alkyl, in particular hydrogen or methyl. In another aspect, the invention relates to compounds of formula I as defined herein before, wherein $R^4$ is hydrogen or $C_{1-7}$-alkyl, in particular hydrogen or methyl. More particularly, both $R^3$ and $R^4$ are hydrogen. In another particular aspect, both $R^3$ and $R^4$ are methyl.

In a further aspect, provided are compounds of formula I, wherein X is $CR^7$ and $R^7$ is selected from the group consisting of hydrogen, halogen, $C_{1-7}$-alkyl and $C_{1-7}$-alkoxy. More particularly, $R^7$ is hydrogen or halogen. In particular, halogen is chloro.

In another aspect, provided are compounds of formula I, wherein X is N.

In a further aspect, the invention relates to compounds of formula I, wherein $R^5$ is selected from the group consisting of hydrogen, halogen and $C_{1-7}$-alkyl. More particularly, $R^5$ is hydrogen, chloro, fluoro or methyl.

In another aspect, provided are compounds of formula I, wherein $R^6$ is selected from the group consisting of hydrogen, halogen and $C_{1-7}$-alkoxy. In particular, $R^6$ is hydrogen, chloro or methoxy.

Particular compounds of the invention are the following:
2-amino-8-(1,4-dihydroquinazolin-2-yl)-N,N-dipropyl-3H-1-benzazepine-4-carboxamide,
2-amino-8-(1,4-dihydropyrido[3,4-d]pyrimidin-2-yl)-N,N-dipropyl-3H-1-benzazepine-4-carboxamide,
2-amino-N-(cyclopropylmethyl)-8-(1,4-dihydroquinazolin-2-yl)-N-propyl-3H-1-benzazepine-4-carboxamide,
2-amino-8-(1,4-dihydroquinazolin-2-yl)-N-isobutyl-N-propyl-3H-1-benzazepine-4-carboxamide,
2-amino-8-(5-chloro-1,4-dihydroquinazolin-2-yl)-N,N-dipropyl-3H-1-benzazepine-4-carboxamide,
2-amino-8-(7-chloro-1,4-dihydroquinazolin-2-yl)-N,N-dipropyl-3H-1-benzazepine-4-carboxamide,
2-amino-8-(4,4-dimethyl-1H-quinazolin-2-yl)-N,N-dipropyl-3H-1-benzazepine-4-carboxamide,
2-amino-8-(6-chloro-1,4-dihydroquinazolin-2-yl)-N,N-dipropyl-3H-1-benzazepine-4-carboxamide,
2-amino-8-(5-methyl-1,4-dihydroquinazolin-2-yl)-N,N-dipropyl-3H-1-benzazepine-4-carboxamide,
2-amino-8-(5-fluoro-1,4-dihydroquinazolin-2-yl)-N,N-dipropyl-3H-1-benzazepine-4-carboxamide, and
2-amino-8-(6-methoxy-1,4-dihydroquinazolin-2-yl)-N,N-dipropyl-3H-1-benzazepine-4-carboxamide.

A further aspect of the present invention is the process for the manufacture of compounds of formula I as defined above, which process comprises a) coupling a compound of the formula II

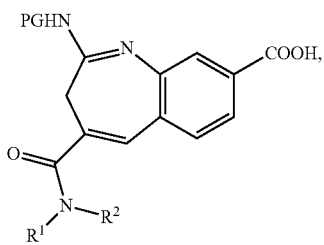

wherein $R^1$ and $R^2$ are as defined in claim 1 and PG is a protecting group, with a compound of the formula III

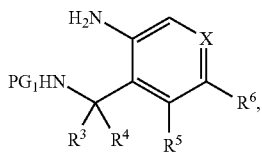

wherein X and $R^3$, $R^4$, $R^5$ and $R^6$ are as defined in claim 1 and $PG_1$ is a protecting group, under basic conditions in the presence of a coupling agent and removing the protecting groups PG and $PG_1$ under acidic conditions to obtain a compound of the formula I

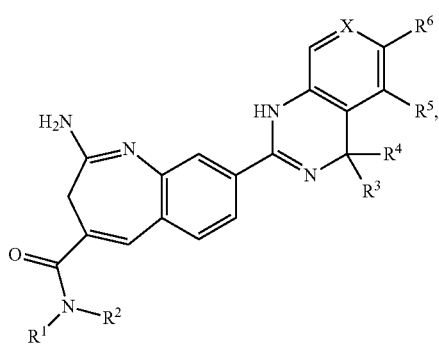

wherein X and $R^1$ to $R^6$ are as defined in claim 1, and, if desired, converting the compound obtained into a pharmaceutically acceptable salt.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

In particular, a suitable protecting group PG is an amino-protecting group selected from Boc (tert-butoxycarbonyl), benzyl (Bz) and benzyloxycarbonyl (Cbz). In particular, the protecting group is Boc.

"Removing the protecting group PG under acidic conditions" means treating the protected compound with acids in a suitable solvent, for instance trifluoroacetic acid (TFA) in a solvent such as dichloromethane (DCM) can be employed.

A suitable "coupling agent" for the reaction of compounds of formula II with amines of formula III is selected from the group consisting of N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazole-N,N,N',N'-tetramethyl-uronium-hexafluoro-phosphate (HBTU) or O-benzotriazol-1-yl-N,N,N',N'-tetramethyluronium tetrafluoroborate (TBTU). In particular, the coupling agent is TBTU. Suitable bases include triethylamine, N-methylmorpholine and, particularly, diisopropylethylamine.

"Under basic conditions" means the presence of a base, in particular a base selected from the group consisting of triethylamine, N-methylmorpholine and, particularly, diisopropylethylamine. Typically, the reaction is carried out in inert solvents such as dimethylformamide or dichloromethane at room temperature.

The invention further relates to compounds of formula I as defined above obtainable according to a process as defined above.

The compounds of the present invention can be prepared by any conventional means. Suitable processes for synthesizing these compounds as well as their starting materials are provided in the schemes below and in the examples. All substituents, in particular, $R^1$ to $R^4$ are as defined above unless otherwise indicated. Furthermore, and unless explicitly otherwise stated, all reactions, reaction conditions, abbreviations and symbols have the meanings well known to a person of ordinary skill in organic chemistry.

A general synthetic route for preparing the compounds of formula I is shown in Scheme 1 below. A symbolizes an aryl ring or a heteroaryl ring.

Scheme 1

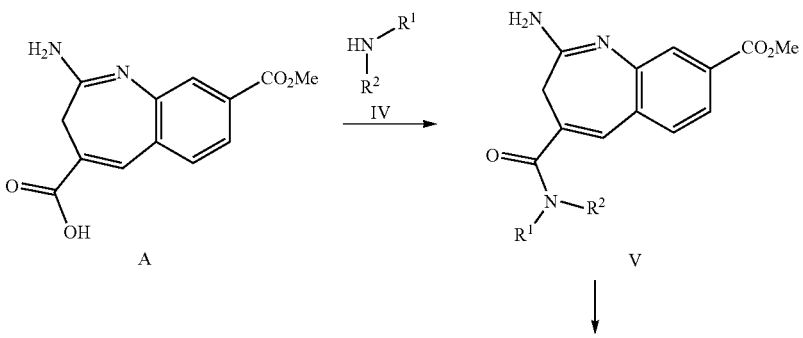

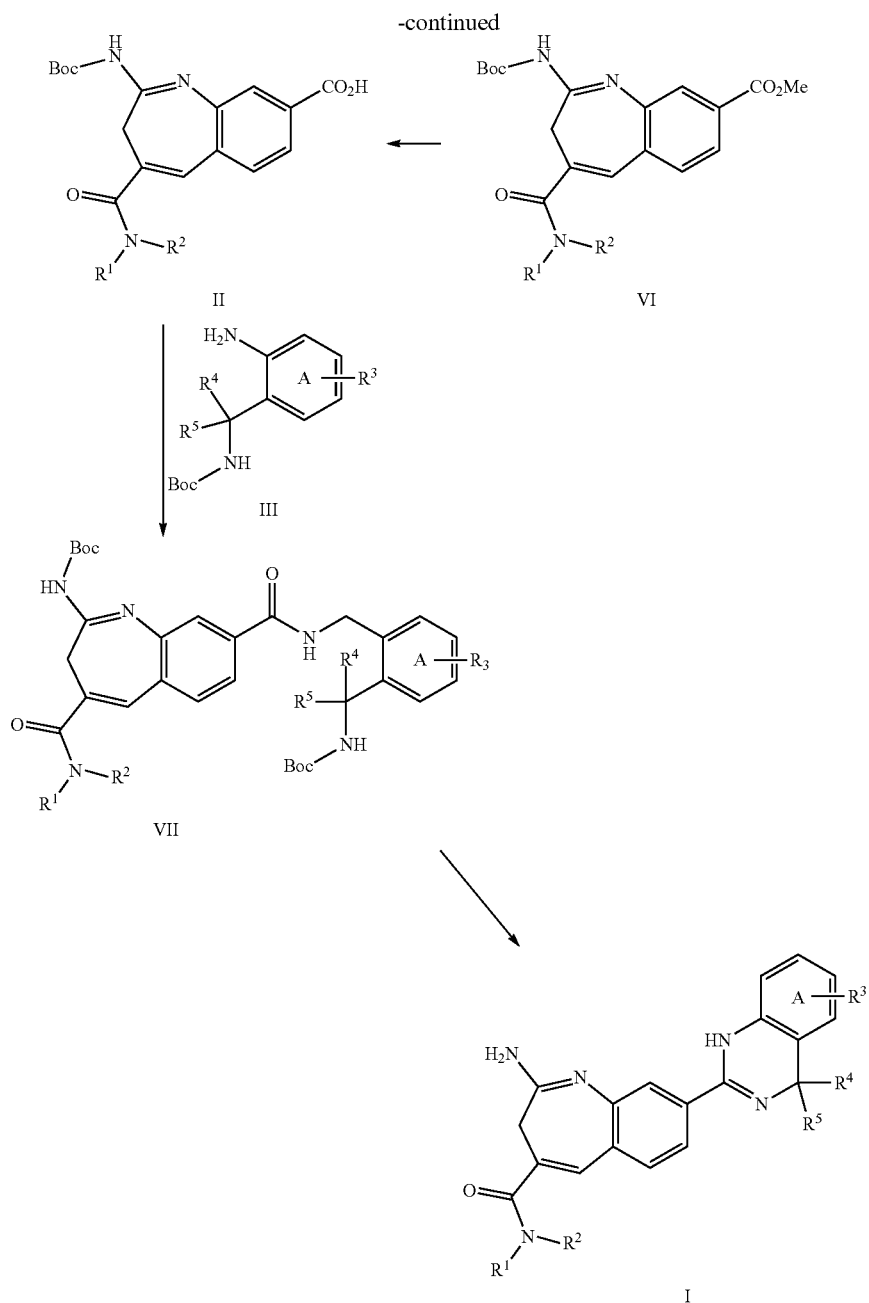

Compounds of formula I can be prepared according to Scheme 1. A coupling reaction between carboxylic acid A and a selected amine IV gives the amide of formula V, which is then protected with an amino protecting group such as Boc to obtain a compound of formula VI. Hydrolysis of the compound of formula VI leads to a carboxylic acid of formula II. The carboxylic acid of formula II is then coupled with a selected aryl or heteroarylamine III to obtain an amide of formula VII. Finally, the compound of formula I is obtained by deprotection of the amino protecting group (e.g. Boc) and in situ cyclization of the amide of formula VII. In some cases, the compound of formula VII may contain an additional acid labile protection group originated from amine IV or amine III, like Boc or TBS, which will be removed also in the final deprotection step.

A coupling reagent, like HBTU, is used to couple the carboxylic acid of formula A and a selected amine IV in the presence of a base, like DIPEA, in a solvent like DCM at ambient or elevated temperature to give a compound of formula V.

Then, the compound of formula V is protected with an amino protecting group, in particular with Boc, to provide a compound of formula VI.

The compound of formula VI is hydrolyzed by a base, in particular LiOH, in a suitable solvent, for example a mixed solvent like THF/MeOH/H$_2$O, at ambient or elevated temperature to obtain a carboxylic acid of formula II.

The carboxylic acid of formula II is then reacted with a selected arylamine or heteroarylamine of formula III under the assistance of a suitable coupling reagent, in particular HATU, in a solvent like DCM and in the presence of a base, in particular DIPEA, at ambient or elevated temperature to result in a compound of formula VII.

Finally, a compound of formula I is obtained by treating the compound of formula VII with TFA in dichloromethane (Boc deprotection and in situ cyclization) and subsequent purification by prep-HPLC.

If one of the starting materials contains one or more functional groups which are not stable or are reactive under the reaction conditions of one or more reaction steps, appropriate protecting groups (PG) (as described e.g. in T. W. Greene et al., Protective Groups in Organic Chemistry, John Wiley and Sons Inc. New York 1999, 3rd edition) can be introduced before the critical step applying methods well known in the art. Such protecting groups can be removed at a later stage of the synthesis using standard methods known in the art. Besides of the Boc protection group at amidine, a compound of formula VII also contains an additional acid labile protection group, like Boc or TBS originated from amine II, which will be also removed in this step.

If one or more compounds of the formula contain chiral centers, compounds of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

As described herein before, the compounds of formula I of the present invention can be used as medicaments for the treatment of diseases which are mediated by TLR agonists, in particular for the treatment of diseases which are mediated by TLR8 agonists.

The compounds defined in the present invention are agonists of TLR8 receptors in cellular assays in vitro. Accordingly, the compounds of the present invention are expected to be potentially useful agents in the treatment of diseases or medical conditions that may benefit from the activation of the immune system via TLR8 agonists. They are useful in the treatment or prevention of diseases such as cancer, autoimmune diseases, inflammation, sepsis, allergy, asthma, graft rejection, graft-versus-host disease, immunodeficiencies, and infectious diseases.

In more detail, the compounds of formula I of the present invention are useful in oncology, i.e. they may be used in the treatment of common cancers including bladder cancer, head and neck cancer, prostate cancer, colorectal cancer, kidney cancer, breast cancer, lung cancer, ovarian cancer, cervical cancer, liver cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention (e.g. vaccination) and treatment of metastatic cancer and tumor recurrences, and paraneoplastic syndromes.

The compounds of formula I of the present invention are also useful in the treatment of autoimmune diseases. An "autoimmune disease" is a disease or disorder arising from and directed against an individual's own tissues or organs or a co-segregate or manifestation thereof or resulting condition therefrom. "Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). In a particular aspect, the autoimmune disease is associated with the skin, muscle tissue, and/or connective tissue.

Particular autoimmune diseases include autoimmune rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases, ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)), allergic conditions and responses, food allergies, drug allergies, insect allergies, rare allergic disorders such as mastocytosis, allergic reaction, eczema including allergic or atopic eczema, asthma such as bronchial asthma and auto-immune asthma, conditions involving infiltration of myeloid cells and T cells and chronic inflammatory responses:

The compounds of formula I of the present invention are also useful in the treatment of infectious diseases. Thus, they may be useful in the treatment of viral diseases, in particular for diseases caused by infection with viruses selected from the group consisting of papilloma viruses, such as human papilloma virus (HPV) and those that cause genital warts, common warts and plantar warts, herpes simplex virus (HSV), molluscum contagiosum, hepatitis B virus (HBV), hepatitis C virus (HCV), Dengue virus, variola virus, human immunodeficiency virus (HIV), cytomegalovirus (CMV), varicella zoster virus (VZV), rhinovirus, enterovirus, adenovirus, coronavirus (e.g. SARS), influenza, mumps and parainfluenza.

They may also be useful in the treatment of bacterial diseases, in particular for diseases caused by infection with bacteria selected from the group consisting of mycobacterium such as mycobacterium tuberculosis, mycobacterium avium and mycobacterium leprae. The compounds of formula I of the present invention may further be useful in the treatment of other infectious diseases, such as chlamydia, fungal diseases, in particular fungal diseases selected from the group consisting of candidiasis, aspergillosis and cryptococcal meningitis, and parasitic diseases such as Pneumocystis carnii, pneumonia, cryptosporidiosis, histoplasmosis, toxoplasmosis, trypanosome infection and leishmaniasis.

Thus, the expression "diseases which are mediated by TLR8 agonists" means diseases which may be treated by activation of the immune system with TLR8 agonists such as cancer, autoimmune diseases, inflammation, sepsis, allergy, asthma, graft rejection, graft-versus-host disease, immunodeficiencies, and infectious diseases. In particular, the expression "diseases which are mediated by TLR agonists" means cancer, autoimmune diseases, inflammation, sepsis, allergy, asthma, graft rejection, graft-versus-host disease, immunodeficiencies, and infectious diseases.

In a particular aspect, the expression "which are mediated by TLR8 agonists" relates to cancer selected from the group consisting of bladder cancer, head and neck cancer, liver cancer, prostate cancer, colorectal cancer, kidney cancer, breast cancer, lung cancer, ovarian cancer, cervical cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention (e.g. vaccination) and treatment of metastatic cancer and tumor recurrences, and paraneoplastic syndromes.

The invention also relates to pharmaceutical compositions comprising a compound of formula I as defined above and a pharmaceutically acceptable carrier and/or adjuvant. More specifically, the invention relates to pharmaceutical compositions useful for the treatment of diseases which are which are mediated by TLR8 agonists.

Further, the invention relates to compounds of formula I as defined above for use as therapeutically active substances, particularly as therapeutically active substances for the treatment of diseases which are which are mediated by TLR8 agonists. In particular, the invention relates to compounds of formula I for use in the treatment of cancers or autoimmune diseases or infectious diseases selected from the group consisting of viral diseases, bacterial diseases, fungal diseases and parasitic diseases.

In another aspect, the invention relates to a method for the treatment a of diseases which are mediated by TLR8 agonists, which method comprises administering a therapeutically active amount of a compound of formula I to a human being or animal. In particular, the invention relates to a method for the treatment of cancers and infectious diseases selected from the group consisting of viral diseases, bacterial diseases, fungal diseases and parasitic diseases.

The invention further relates to the use of compounds of formula I as defined above for the treatment of diseases which are mediated by TLR8 agonists.

In addition, the invention relates to the use of compounds of formula I as defined above for the preparation of medicaments for the treatment of diseases which are mediated by TLR8 agonists. In particular, the invention relates to the use of compounds of formula I as defined above for the preparation of medicaments for the treatment of cancers or autoimmune diseases or infectious diseases selected from the group consisting of viral diseases, bacterial diseases, fungal diseases and parasitic diseases.

In a further aspect, compounds of formula I can be in combination with one or more additional treatment modalities in a regimen for the treatment of cancer.

Combination therapy encompasses, in addition to the administration of a compound of the invention, the adjunctive use of one or more modalities that are effective in the treatment of cancer. Such modalities include, but are not limited to, chemotherapeutic agents, immunotherapeutics, anti-angiogenic agents, cytokines, hormones, antibodies, polynucleotides, radiation and photodynamic therapeutic agents. In a specific aspect, combination therapy can be used to prevent the recurrence of cancer, inhibit metastasis, or inhibit the growth and/or spread of cancer or metastasis. As used herein, "in combination with" means that the compound of formula I is administered as part of a treatment regimen that comprises one or more additional treatment modalities as mentioned above. The invention thus also relates to a method for the treatment of cancer, which method comprises administering a therapeutically active amount of a compound of formula I in combination with one or more other pharmaceutically active compounds to a human being or animal.

Compounds of formula I can be used alone or in combination with one or more additional treatment modalities in treating autoimmune diseases.

Combination therapy encompasses, in addition to the administration of a compound of the invention, the adjunctive use of one or more modalities that aid in the prevention or treatment of autoimmune diseases. Such modalities include, but are not limited to, chemotherapeutic agents, immunotherapeutics, anti-angiogenic agents, cytokines, hormones, antibodies, polynucleotides, radiation and photodynamic therapeutic agents. As used herein, "in combination with" means that the compound of formula I is administered as part of a treatment regimen that comprises one or more additional treatment modalities as mentioned above. The invention thus also relates to a method for the treatment of autoimmune diseases, which method comprises administering a therapeutically active amount of a compound of formula I in combination with one or more other pharmaceutically active compounds to a human being or animal.

In a further aspect, compounds of formula I can be used alone or in combination with one or more additional treatment modalities in treating infectious diseases.

Combination therapy encompasses, in addition to the administration of a compound of the invention, the adjunctive use of one or more modalities that aid in the prevention or treatment of infectious diseases. Such modalities include, but are not limited to, antiviral agents, antibiotics, and anti-fungal agents. As used herein, "in combination with" means that the compound of formula I is administered as part of a treatment regimen that comprises one or more additional treatment modalities as mentioned above. The invention thus also relates to a method for the treatment of infectious diseases, which method comprises administering a therapeutically active amount of a compound of formula I in combination with one or more other pharmaceutically active compounds to a human being or animal.

Pharmacological Test

The following tests were carried out in order to determine the activity of the compounds of formula I:

For TLR8 and TLR7 activity testing, HEK-Blue human TLR8 or TLR7 cells (Invivogen, San Diego, Calif., USA) are used, respectively. These cells are designed for studying the stimulation of human TLR8 or TLR7 by monitoring the activation of NF-κB. A SEAP (secreted embryonic alkaline phosphatase) reporter gene is placed under the control of the IFN-b minimal promoter fused to five NF-κB and AP-1-binding sites. Therefore the reporter expression is regulated by the NF-κB promoter upon stimulation of human TLR8 or TLR7 for 20 hours. The cell culture supernatant SEAP reporter activity was determined using Quanti Blue kit (Invivogen, San Diego, Calif., USA) at a wavelength of 640 nm, a detection medium that turns purple/blue in the presence of alkaline phosphatase. $EC_{50}$ values were determined using Activity Base analysis (ID Business Solution, Limited).

VTX-133 and VTX-135 are two examples described in International Patent Application No. WO 2011/022509 and their activity in HEK-blue human TLR7 and TLR8 cells are shown in Table 1.

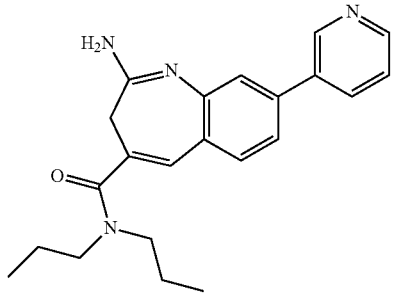

VTX-133

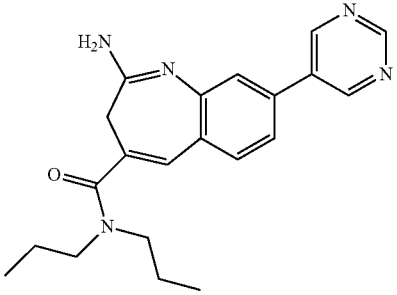

VTX-135

Of note, the new compounds described in this patent have improved cellular potency at TLR8 compared to known TLR8 agonists such as VTX-133 and VTX-135 described in WO 2011022509. In addition these compounds are highly specific towards TLR8 with no appreciable activity towards TLR7. Thus, they are expected to possess advantageous properties compared to combined TLR7/8 agonists due to the more restricted expression pattern of TLR8 resulting in less served side effects when administered systemically.

The compounds according to formula I have an activity ($EC_{50}$ value) in the above assay for human TLR8 in the range of 0.001 μM to 0.03 μM, more particularly of 0.001 μM to 0.015 μM, whereas the activity ($EC_{50}$ value) in the above assay for human TLR7 is greater than 100 μM, meaning the compounds show very high selectivity towards human TLR8.

For example, the following compounds showed the following $EC_{50}$ values in the assay described above:

TABLE 1

| Example | human TLR8 $EC_{50}$ [μM] | human TLR7 $EC_{50}$ [μM] |
|---|---|---|
| VTX-133 | 0.077 | 1.86 |
| VTX-135 | 0.039 | 3.61 |
| 1 | 0.003 | >100 |
| 2 | 0.003 | >100 |
| 3 | 0.006 | >100 |
| 4 | 0.011 | >100 |
| 5 | 0.011 | >100 |
| 6 | 0.009 | >100 |
| 7 | 0.007 | >100 |
| 8 | 0.006 | >100 |
| 9 | 0.001 | >100 |
| 10 | 0.003 | >100 |
| 11 | 0.002 | >100 |

Pharmaceutical Compositions

The compounds of formula I and their pharmaceutically acceptable salts can be used as medicaments, e.g., in the form of pharmaceutical preparations for enteral, parenteral or topical administration. The compounds of formula I and their pharmaceutically acceptable salts may be administered by systemic (e.g., parenteral) or local (e.g., topical or intralesional injection) administration. In some instances, the pharmaceutical formulation is topically, parenterally, orally, vaginally, intrauterine, intranasal, or by inhalation administered. As described herein, certain tissues may be preferred targets for the TLR8 agonist. Thus, administration of the TLR8 agonist to lymph nodes, spleen, bone marrow, blood, as well as tissue exposed to virus, are preferred sites of administration.

In one aspect, the pharmaceutical formulation comprising the compounds of formula I or its pharmaceutically acceptable salts is administered parenterally. Parenteral routes of administration include, but are not limited to, transdermal, transmucosal, nasopharyngeal, pulmonary and direct injection. Parenteral administration by injection may be by any parenteral injection route, including, but not limited to, intravenous (IV), including bolus and infusion (e.g., fast or slow), intraperitoneal (IP). intramuscular (IM), subcutaneous (SC) and intradermal (ID) routes. Transdermal and transmucosal administration may be accomplished by, for example, inclusion of a carrier (e.g., dimethylsulfoxide, DMSO), by application of electrical impulses (e.g., iontophoresis) or a combination thereof. A variety of devices are available for transdermal administration which may be used. Formulations of the compounds of formula I suitable for parenteral administration are generally formulated in USP water or water for injection and may further comprise pH buffers, salts bulking agents, preservatives, and other pharmaceutically acceptable excipients.

Transdermal administration is accomplished by application of a cream, rinse, gel, etc. capable of allowing the TLR8 agonist to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter. Administration via the transdermal and transmucosal routes may be continuous or pulsatile.

Pulmonary administration is accomplished by inhalation, and includes delivery routes such as intranasal, transbronchial and transalveolar routes. Formulations of compounds of formula I suitable for administration by inhalation including, but not limited to, liquid suspensions for forming aerosols as well as powder forms for dry powder inhalation delivery systems are provided. Devices suitable for administration by inhalation include, but are not limited to, atomizers, vaporizers, nebulizers, and dry powder inhalation delivery devices. Other methods of delivering to respiratory mucosa include delivery of liquid formulations, such as by nose drops. Administration by inhalation is preferably accomplished in discrete doses (e.g., via a metered dose inhaler), although delivery similar to an infusion may be accomplished through use of a nebulizer.

The compounds of formula I and pharmaceutically acceptable salts thereof may also be administered orally, e.g., in the form of tablets, coated tablets, dragées, hard and soft gelatine capsules.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples C1 to C3 illustrate typical compositions of the present invention, but serve merely as representative thereof.

EXAMPLE C1

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

EXAMPLE C2

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

EXAMPLE C3

Injection solutions can have the following composition:

| Compound of formula I | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

The following examples serve to illustrate the present invention in more detail. They are, however, not intended to limit its scope in any manner.

EXAMPLES

Abbreviations used therein:

$Boc_2O$=di-tent-butyl dicarbonate, Boc=t-butyl carbamate, calc'd=calculated, $CD_3OD$=deuterated methanol, d=day, DIPEA=N,N-diisopropylethylamine, DCM=dichloromethane, DMAP: 4-dimethylaminopyridine, DMF-DMA: N,N-dimethylformamide dimethyl acetal, EA=ethyl acetate or EtOAc, $EC_{50}$=half maximal effective concentration, h or hr=hour, HBTU=O-(benzotriazol-1-yl)-N,N,N',N'-tetramethyluronium hexafluorophosphate, DMAP=4-dimethylaminopyridine, HATU=(1-[Bis(dimethylamino)methylene]-1H-1,2,3-triazolo[4,5-b]pyridinium 3-oxid hexafluorophosphate), HPLC-UV=high performance liquid chromatography with ultraviolet detector, Hz=hertz, mg=milligram, MHz=megahertz, min=minute(s), mL=milliliter, mm=millimeter, mM=mmol/L, mmol=millimole, MS=mass spectrometry, MW=molecular weight, NMR=nuclear magnetic resonance, PE=petroleum ether, prep-HPLC=preparative high performance liquid chromatography, rt=room temperature, sat.=sat., TBS=tert-butyldimethylsilyl, sxt=sextet, TEA=triethylamine, TFA=trifluoroacetic acid, THF=tetrahydrofuran, μM=micromole/L, μm=micrometer, UV=ultraviolet detector, OD=optical density, TLR8=toll-like receptor 8, TLR7=toll-like receptor 7, NFκB=nuclear factor kappa-light-chain-enhancer of activated B cells, SEAP=secreted embryonic alkaline phosphatase, IFN-β=interferon-beta.

Example A—Preparation of Key Intermediate A

2-Amino-8-methoxycarbonyl-3H-1-benzazepine-4-carboxylic acid

A detailed synthetic route is provided in Scheme 2.

a) Preparation of Compound B

To a solution of methyl 4-methyl-3-nitrobenzoate (100 g, 0.51 mol) in DMF (1 L) was added DMF-DMA (73 g, 0.61 mol). The reaction mixture was heated to 105° C. for 18 hrs. Then the solvent was removed in vacuo to give methyl 4-(2-(dimethylamino)vinyl)-3-nitrobenzoate (compound B, 127 g, crude) which was used in the next step without purification. MS: calc'd 251 (M+H)$^+$, measured 251(M+H)$^+$.

Scheme 2

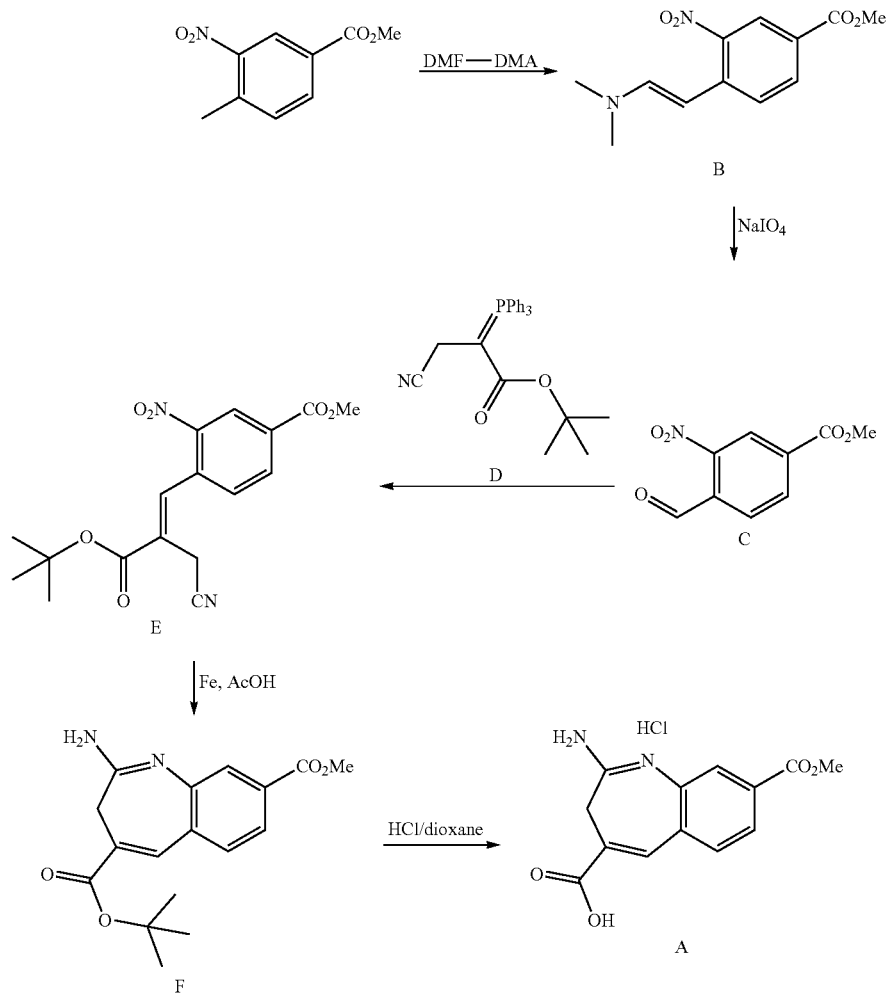

b) Preparation of Compound C

To a solution of NaIO$_4$ (327 g, 1.53 mol) in a mixed solvent of THF (1.3 L) and water (2.0 L) was added a THF (0.7 L) solution of methyl 4-(2-(dimethylamino)vinyl)-3-nitrobenzoate (compound A, 127 g, 0.51 mol) at 10° C. After the reaction mixture was stirred at 25° C. for 18 hrs, the mixture was filtered and then extracted with EA. The organic layer was washed with brine, dried over anhydrous Na$_2$SO$_4$, filtered and concentrated to give the crude product. The crude product was purified by silica gel column chromatography (PE:EA=20:1-10:1) to give methyl 4-formyl-3-nitrobenzoate (compound C, 84 g, 79%) as a yellow solid. MS: calc'd 210 (M+H)$^+$, measured 210 (M+H)$^+$.

c) Preparation of Compound D

To a solution of tent-butyl 2-(triphenylphosphoranylidene)acetate (300 g, 0.797 mol) in EA (2 L) was added 2-bromoacetonitrile (57 g, 0.479 mol) at 25° C. The reaction was heated to reflux for 18 hrs. After it was cooled to ambient temperature, the solid was filtered and the filtrate was concentrated. The residue was purified by triturating from EA and PE (200 mL, 2.5:1) to give the desired product tent-butyl 3-cyano-2-(triphenylphosphoranylidene)propanoate (compound D, 125 g, 63%) as a white solid. MS: calc'd 416 (M+H)$^+$, measured 416 (M+H)$^+$.

d) Preparation of Compound E

To a solution of 4-formyl-3-nitrobenzoate (compound C, 50 g, 0.24 mol) in toluene (600 mL) was added tent-butyl 3-cyano-2-(triphenylphosphoranylidene)propanoate (compound D, 109 g, 0.26 mol) at 25° C. After the reaction mixture was stirred at 25° C. for 18 hrs, it was cooled in ice-bath for 1 hr. The precipitate was collected and dried to give the desired product as a white solid. The filtrate was concentrated and treated with EtOH (120 mL). The undissolved material was filtered and the filtrate was concentrated to give an additional batch of the desired product. These two batches were combined to give methyl 4-(3-(tert-butoxy)-2-(cyanomethyl)-3-oxoprop-1-en-1-yl)-3-nitrobenzoate (compound E, 60 g, 72%). MS: calc'd 347 (M+H)$^+$, measured 347 (M+H)$^+$.

e) Preparation of Compound F

To a solution of methyl 4-(3-(tert-butoxy)-2-(cyanomethyl)-3-oxoprop-1-en-1-yl)-3-nitrobenzoate (compound E, 30 g, 87 mmol) in AcOH (450 mL) was added Fe powder (29.1 g, 520 mmol) at 60° C. After the reaction mixture was heated at 85° C. for 3 hrs, it was filtered through celite and the precipitate was washed with acetic acid. The filtrate was concentrated in vacuo and the residue was carefully basified with aqueous sat. $NaHCO_3$ solution (300 mL). Then EA (600 mL) was added. The mixture was filtered through celite and the precipitate was washed with EA (200 mL). The filtrate was then washed with water, dried over $Na_2SO_4$ and concentrated in vacuo to get 4-tent-butyl 8-methyl 2-amino-3H-benzo[b]azepine-4,8-dicarboxylate (compound F, 25 g, 93%) as a light yellow solid. MS: calc'd 317 $(M+H)^+$, measured 317 $(M+H)^+$.

f) Preparation of Compound A

To a solution of 4-tent-butyl 8-methyl 2-amino-3H-benzo[b]azepine-4,8-dicarboxylate (compound F, 25 g, 80 mmol) in dioxane (400 mL) was added a 1 M solution of HCl in dioxane (600 mL) at 0° C. After the reaction mixture was stirred at 25° C. for 18 hrs, it was concentrated in vacuo to give 2-amino-8-(methoxycarbonyl)-3H-benzo[b]azepine-4-carboxylic acid hydrochloride (compound A, 25 g, crude) which was used in the next step without any purification. MS: calc'd 261 $(M+H)^+$, measured 261 $(M+H)^+$.

Example B—Preparation of Key Intermediate J 2-(tert-butoxycarbonylamino)-4-(dipropylcarbamoyl)-3H-1-benzazepine-8-carboxylic acid A detailed synthetic route is provided in Scheme 3.

g) Preparation of Compound G

To a mixture of 2-amino-8-(methoxycarbonyl)-3H-benzo[b]azepine-4-carboxylic acid hydrochloride (compound A, 19 g, 64 mmol), HBTU (29 g, 77 mmol), DIPEA (33 g, 257 mmol) in DMF (400 mL) was added di-n-propylamine (13 g, 128 mmol) at 0° C. After the reaction mixture was stirred at 20° C. for 2 hrs, it was quenched with sat. $NH_4Cl$ (500 mL), diluted with $H_2O$ (1 L), and extracted with EA (300 mL×3). The combined organic layers were washed with brine (300 mL×2), dried over $Na_2SO_4$ and concentrated to give the crude product. The crude product was purified by silica gel column chromatography (PE:EA=1:1) to give methyl 2-amino-4-(dipropylcarbamoyl)-3H-benzo[b]azepine-8-carboxylate (compound G, 18 g, 82%) as a yellow solid. MS: calc'd 344 $(M+H)^+$, measured 344 $(M+H)^+$.

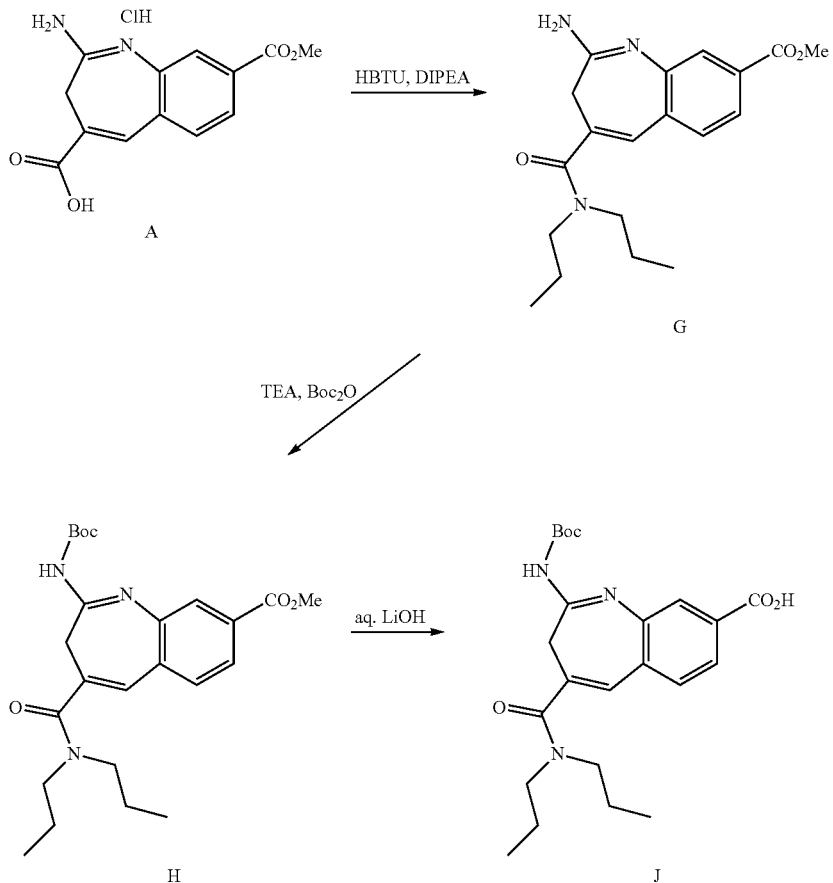

Scheme 3 h) Preparation of Compound H

To a mixture of methyl 2-amino-4-(dipropylcarbamoyl)-3H-benzo[b]azepine-8-carboxylate (compound G, 18 g, 53 mmol) and TEA (16 g, 157 mmol) in DCM (300 mL) was added Boc$_2$O (17 g, 79 mmol) at 0° C. After the mixture was stirred at 20° C. for 16 hrs, it was quenched with sat. NH$_4$Cl (300 mL), diluted with H$_2$O (500 mL), and extracted with DCM (100 mL×3). The combined organic layers were washed with brine (100 mL×2), dried over Na$_2$SO$_4$ and concentrated to give the crude product. The crude product was purified by silica gel column chromatography (PE:EA=3:1) to give methyl 2-((tert-butoxycarbonyl)amino)-4-(dipropylcarbamoyl)-3H-benzo[b]azepine-8-carboxylate (compound H, 21 g, yield: 91%) as a yellow solid. MS: calc'd 444 (M+H)$^+$, measured 444 (M+H)$^+$.

i) Preparation of Compound J

To a solution of methyl 2-((tert-butoxycarbonyl)amino)-4-(dipropylcarbamoyl)-3H-benzo[b]azepine-8-carboxylate (compound H, 5.0 g, 11.3 mmol) in THF/H$_2$O (1/1, 100 mL,) was added aq. LiOH solution (1 M, 17 mL, 17 mmol) at 0° C. Then the mixture was warmed to 25° C. and stirred for 6 hrs. The mixture was poured into ice-water (150 mL), acidified with aq. citric acid (5%) to pH=5 and extracted with EtOAc (100 mL×3). The combined organic layers were washed with brine (100 mL×2), dried over Na$_2$SO$_4$ and concentrated in vacuo to give 2-(tert-butoxycarbonylamino)-4-(dipropylcarbamoyl)-3H-1-benzazepine-8-carboxylic acid (compound J, 4.0 g, 83.3%) as a yellow solid. $^1$H NMR (400MHz, DMSO-d$_6$) δ ppm=7.78-7.72 (m, 1H), 7.64 (dd, J=1.5, 8.0 Hz, 1H), 7.55 (d, J=8.3 Hz, 1H), 6.93-6.89 (m, 1H), 3.14 (s, 6H), 1.54 (br. s., 4H), 1.44 (s, 9H), 0.80 (br. s., 6H). MS: calc'd 430 (M+H)$^+$, measured 430 (M+H)$^+$.

Example 1

2-Amino-8-(1,4-dihydroquinazolin-2-yl)-N,N-dipropyl-3H-1-benzazepine-4-carboxamide

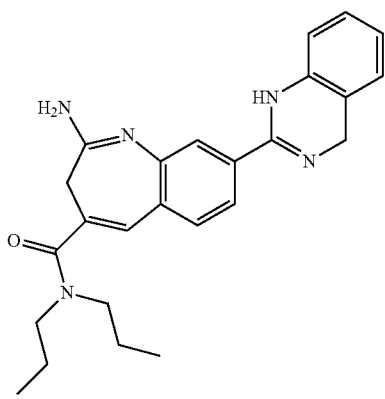 [SMILES: CCCN(CCC)C(=O)C1=Cc2ccc(C3=NCc4ccccc4N3)cc2N=C(N)C1]

Example 1 can be prepared according to general procedure in scheme 1. A detailed synthetic route is provided in Scheme 4.

Scheme 4

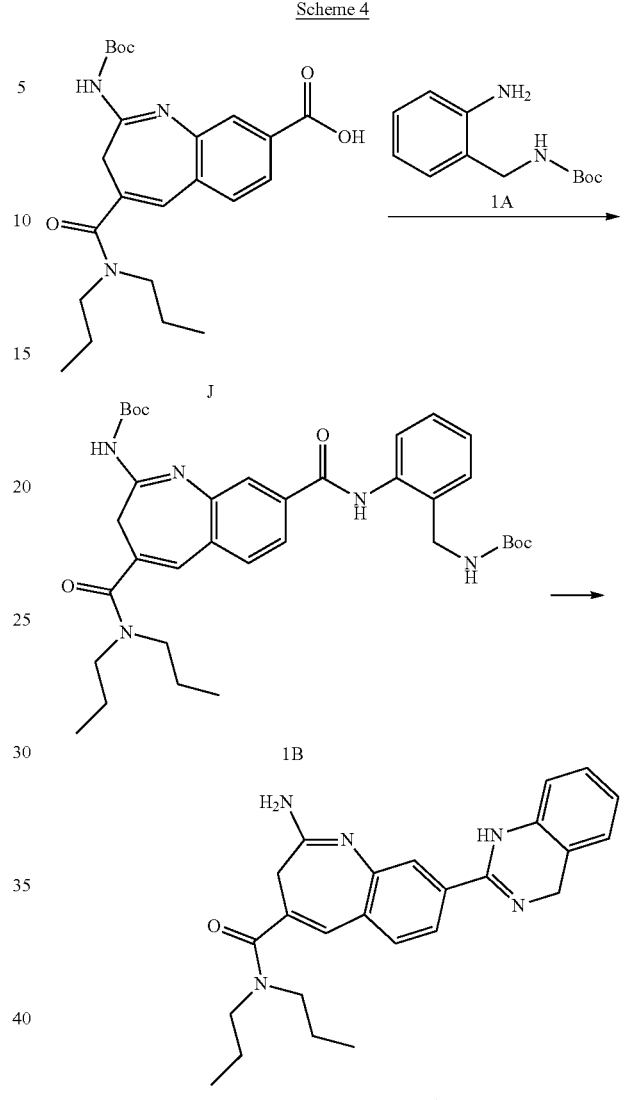

Preparation of compound 1B:

To a solution of 2-(tert-butoxycarbonylamino)-4-(dipropylcarbamoyl)-3H-1-benzazepine-8-carboxylic acid (compound J, 200 mg, 0.465 mmol) in DMF (4.0 mL) was added HATU (177 mg, 0.550 mmol), DIPEA (84 mg, 0.60 mmol) and tent-butyl N-[(2-aminophenyl)methyl]-carbamate (compound 1A, 122 mg, 0.55 mmol). The solution was stirred at 50° C. for 24 hrs. Water (10 mL) was added and the mixture was extracted with EA(10 mL×2). The organic layer was washed by brine (10 mL×2), dried over Na$_2$SO$_4$ and concentrated in vacuo to give the crude product. The residue was purified by prep-TLC to give tent-butyl N-[[2-[[2-(tert-butoxycarbonyl-amino)-4-(dipropylcarbamoyl)-3H-1-benzazepine-8-carbonyl]amino]phenyl]methyl]carbamate (compound 1B, 15 mg) as a yellow solid. MS: calc'd 634 (M+H)$^+$, measured 634 (M+H)$^+$.

Preparation of Example 1:

To a solution of tent-butyl N-[[2-[[2-(tert-butoxycarbonylamino)-4-(dipropylcarbamoyl)-3H-1-benzazepine-8-carbonyl]amino]phenyl]methyl]carbamate (compound 1B, 15 mg, 0.023 mmol) in DCM (1.0 ml) was added TFA (0.3 mL). The reaction was stirred at 20° C. for 2 hrs. Then the reaction mixture was concentrated and the residue was purified by preparative HPLC to give 2-amino-8-(1,4-dihydroquinazolin-2-yl)-N,N-dipropyl-3H-1-benzazepine-4-carboxamide (Example 1, 12 mg) as a yellow solid. ¹H NMR (400 MHz, MeOD) δ ppm=7.89-7.85 (m, 3H), 7.42-7.36 (m, 2H), 7.29-7.25 (m, 2H), 7.16 (s, 1H), 5.01 (s, 2H), 3.48 (m, 4 H), 3.41 (s, 2H), 1.74-1.69 (m., 4H), 1.00-0.93 (m, 6H). MS: calc'd 416 (M+H)+, measured 416 (M+H)+.

Example 2

2-Amino-8-(1,4-dihydropyrido[3,4-d]pyrimidin-2-yl)-N,N-dipropyl-3H-1-benzazepine-4-carboxamide

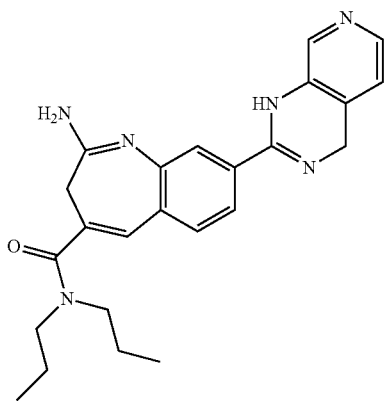 [SMILES: CCCN(CCC)C(=O)C1=Cc2ccc(C3=NCc4ccncc4N3)cc2N=C(N)C1]

The title compound was prepared in analogy to Example 1 by using tent-butyl ((3-aminopyridin-4-yl)methyl)carbamate instead of tent-butyl 2-aminobenzylcarbamate. Example 2 was obtained (16 mg) as a yellow solid. ¹H NMR (400 MHz, MeOD) δ ppm=8.44 (m, 2H), 7.84-7.80 (m, 3H), 7.33-7.27 (m, 1H), 7.01 (s, 1H), 4.94 (s, 2H), 3.41-3.16 (m, 6H), 1.75-1.55 (m., 4H), 1.15-0.8 (m, 6H). MS: calc'd 417 (M+H)+, measured 417 (M+H)+.

Example 3

2-Amino-N-(cyclopropylmethyl)-8-(1,4-dihydroquinazolin-2-yl)-N-propyl-3H-1-benzazepine-4-carboxamide

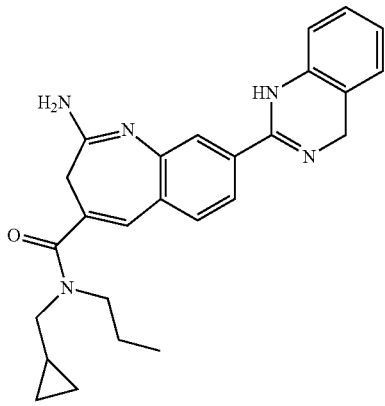 [SMILES: CCCN(CC1CC1)C(=O)C1=Cc2ccc(C3=NCc4ccccc4N3)cc2N=C(N)C1]

A detailed synthetic route is provided in Scheme 5.

Scheme 5

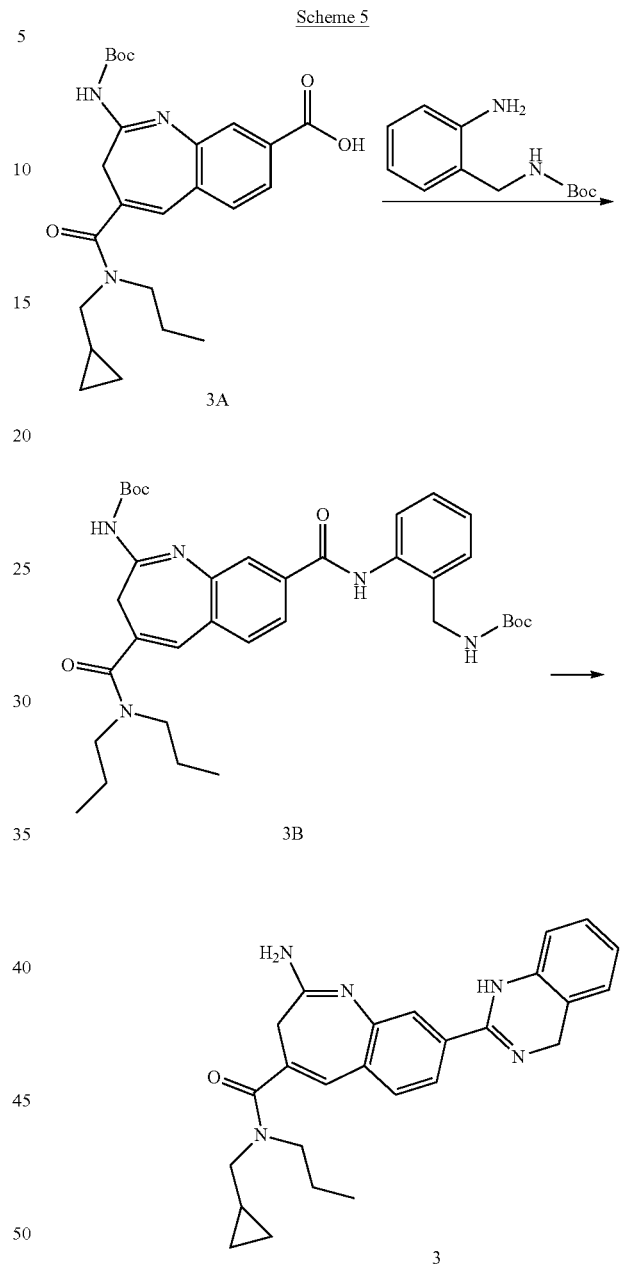

The title compound was prepared in analogy to Example 1 by using 2-((tert-butoxycarbonyl)amino)-4-((cyclopropylmethyl)(propyl)carbamoyl)-3H-benzo[b]azepine-8-carboxylic acid (compound 3A) instead of 2-(tert-butoxycarbonylamino)-4-(dipropylcarbamoyl)-3H-1-benzazepine-8-carboxylic acid (compound J). Example 3 was obtained (2 mg) as a white solid. ¹H NMR (400 MHz, MeOD) δ ppm=7.87-7.85 (m, 3H), 7.42-7.36 (m, 2H), 7.30-7.24 (m, 2H), 7.17 (s, 1H), 5.04 (s, 2H), 3.61-3.59 (m, 2 H), 3.44-3.41 (m, 4H), 1.76-1.74 (m, 2H), 1.31 (br s, 1H), 1.11-0.97 (br s, 3H), 0.64 (br s, 2H), 0.31 (br s, 2H). MS: calc'd 428 (M+H)+, measured 428 (M+H)+.

Preparation of compound 3A:

The title compound was prepared in analogy to key intermediate J of Example B by using N-(cyclopropylmethyl)propan-1-amine instead of di-n-propylamine.

Example 4

2-Amino-8-(1,4-dihydroquinazolin-2-yl)-N-isobutyl-N-propyl-3H-1-benzazepine-4-carboxamide

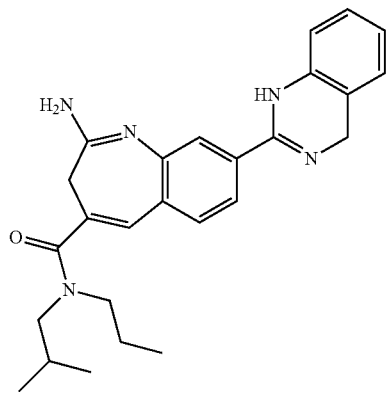 [SMILES: CCCN(CC(C)C)C(=O)C1=Cc2ccc(C3=NCc4ccccc4N3)cc2N=C(N)C1]

The title compound was prepared in analogy to Example 3 by using 2-methyl-N-propylpropan-1-amine instead of N-(cyclopropylmethyl)propan-1-amine. Example 4 was obtained (4.5 mg) as a yellow solid. $^1$H NMR (400MHz, MeOD) δ ppm=7.87-7.83 (m, 3H), 7.35-7.27 (m, 4H), 7.14 (s, 1H), 5.03 (s, 2H), 3.38 (br s, 6H), 1.75-1.6 (m, 3H), 0.92 (br s, 9H). MS: calc'd 430 (M+H)$^+$, measured 430 (M+H)$^+$.

Example 5

2-Amino-8-(5-chloro-1,4-dihydroquinazolin-2-yl)-N,N-dipropyl-3H-1-benzazepine-4-carboxamide

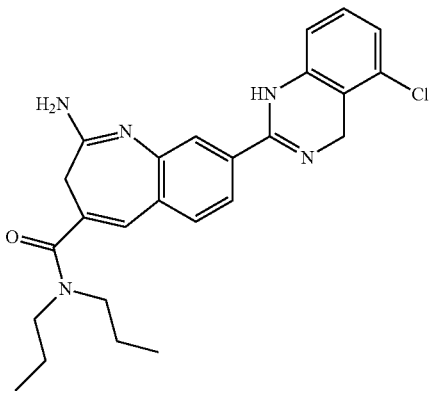 [SMILES: CCCN(CCC)C(=O)C1=Cc2ccc(C3=NCc4c(Cl)cccc4N3)cc2N=C(N)C1]

The title compound was prepared in analogy to Example 1 by using tent-butyl 2-amino-6-chlorobenzylcarbamate (compound 5C) instead of tent-butyl N-[(2-aminophenyl)methyl]-carbamate. Example 5 was obtained (19 mg) as a white solid. $^1$H NMR (400 MHz, MeOD) δ ppm=7.76-7.72 (m, 3H), 7.79-7.78 (m, 2H), 7.03 (s, 2H), 4.92 (s, 2H), 3.37 (br s, 6H), 1.61-1.59 (m., 4H), 1.00-0.93 (m, 6H). MS: calc'd 450 (M+H)$^+$, measured 450 (M+H)$^+$.

The preparation of compound 5C is shown in scheme 6.

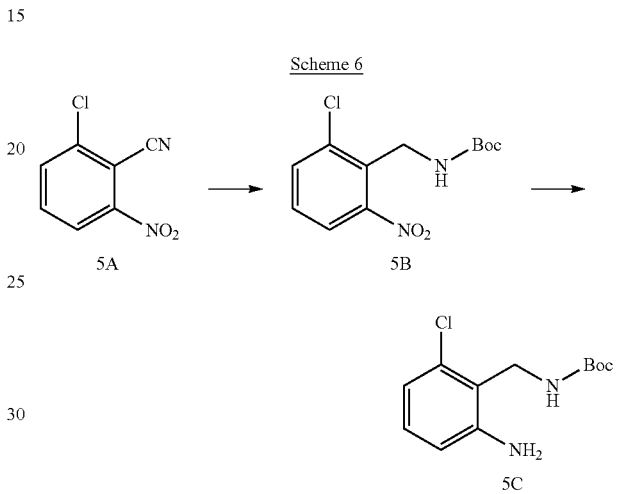

To a solution of 2-chloro-6-nitrobenzonitrile (compound 5A, 2.0 g, 10.98 mmol) in THF (20 mL) was added BH$_3$.THF (33 mL, 32.9 mmol). The solution was refluxed for 3 hrs. The reaction solution was cooled under ice-bath and then MeOH (20 mL) was added dropwise. The solution was stirred for 30 min and then Boc$_2$O (2.63 g, 12.1 mmol) was added. The solution was stirred at 20° C. for 3 hrs. After the reaction solution was concentrated in vacuo, the residue was purified by column chromatography (PE/EtOAc=20/1~5/1) to give crude tent-butyl 2-chloro-6-nitrobenzylcarbamate (compound 5B, 1.4 g, 44.5%) as yellow oil, which was used for the next step directly. MS: calc'd 287 (M+H)$^+$, measured 287 (M+H)$^+$.

To a solution of tent-butyl 2-chloro-6-nitrobenzylcarbamate (compound 5B, 1.4 g, 4.9 mmol) in MeOH (70 mL) was added NH$_4$Cl (3.6 g, 68.5 mmol) and Zn (2.79 g, 44.0 mmol). The solution was stirred at 20° C. for 2 hrs. The reaction solution was concentrated in vacuo. Water(30 mL) was added, and the mixture was extracted with EA(30 mL). The organic layer was washed with brine, dried over anhydrous Na$_2$SO$_4$ and concentrated in vacuo to give tent-butyl 2-amino-6-chlorobenzylcarbamate (compound 5C, 800 mg, 64%) as a yellow solid, which was used for the next step directly. MS: calc'd 257 (M+H)$^+$, measured 257 (M+H)$^+$.

Example 6

2-Amino-8-(7-chloro-1,4-dihydroquinazolin-2-yl)-N,N-dipropyl-3H-1-benzazepine-4-carboxamide

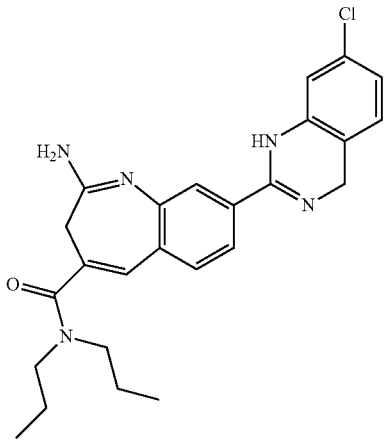 [SMILES: CCCN(CCC)C(=O)C1=Cc2ccc(C3=NCc4ccc(Cl)cc4N3)cc2N=C(N)C1]

The title compound was prepared in analogy to Example 5 by using tent-butyl 2-amino-4-chlorobenzylcarbamate instead of tent-butyl N-[(2-aminophenyl)methyl]carbamate. Example 5 was obtained (5 mg) as a white solid. $^1$H NMR (400 MHz, MeOD) δ ppm=7.88-7.84 (m, 3H), 7.35-7.28 (m, 3H), 7.15 (s, 1H), 5.01 (s, 2H), 3.48-3.40 (m, 6 H), 1.75-1.68 (m., 4H), 0.96 (br s, 6H). MS: calc'd 450 (M+H)$^+$, measured 450 (M+H)$^+$.

Example 7

2-Amino-8-(4,4-dimethyl-1H-quinazolin-2-yl)-N,N-dipropyl-3H-1-benzazepine-4-carboxamide

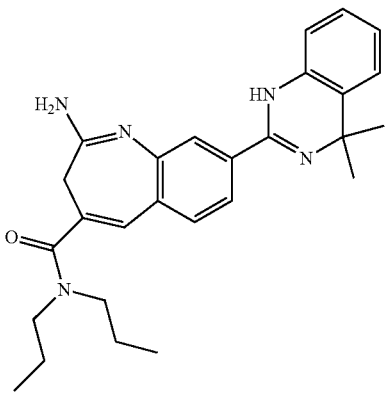 [SMILES: CCCN(CCC)C(=O)C1=Cc2ccc(C3=NC(C)(C)c4ccccc4N3)cc2N=C(N)C1]

The title compound was prepared in analogy to Example 1 by using 2-(2-aminopropan-2-yl)aniline instead of tent-butyl N-[(2-aminophenyl)methyl]carbamate. Example 7 was obtained (18 mg) as a white solid. $^1$H NMR (400 MHz, MeOD) δ ppm=7.86 (brs, 3H), 7.51-7.25 (m, 4H), 7.17 (s, 1H), 3.55-3.40 (m, 6 H),1.86 (s, 6H), 1.73-1.71 (m, 4H), 0.97 (br s, 6H). MS: calc'd 444 (M+H)$^+$, measured 444 (M+H)$^+$.

Example 8

2-Amino-8-(6-chloro-1,4-dihydroquinazolin-2-yl)-N,N-dipropyl-3H-1-benzazepine-4-carboxamide

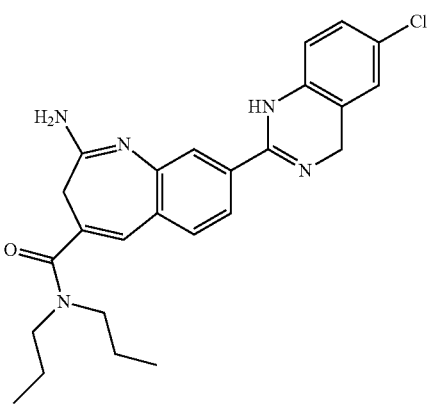 [SMILES: CCCN(CCC)C(=O)C1=Cc2ccc(C3=NCc4cc(Cl)ccc4N3)cc2N=C(N)C1]

The title compound was prepared in analogy to Example 5 by using tent-butyl 2-amino-5-chlorobenzylcarbamate instead of tent-butyl 2-amino-6-chlorobenzylcarbamate. Example 8 was obtained (6 mg) as a white solid. $^1$H NMR (400 MHz, MeOD) δ ppm=7.86-7.83 (m, 3H), 7.42-7.23 (m, 3H), 7.15 (s, 1H), 5.02 (s, 2H), 3.49-3.39 (m, 6 H), 1.74-1.69 (m., 4H), 1.00-0.92 (br s, 6H). MS: calc'd 450 (M+H)$^+$, measured 450 (M+H)$^+$.

Example 9

2-Amino-8-(5-methyl-1,4-dihydroquinazolin-2-yl)-N,N-dipropyl-3H-1-benzazepine-4-carboxamide

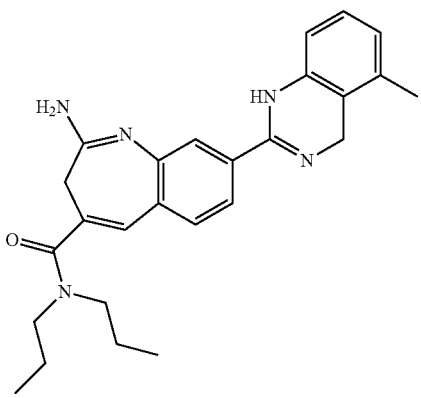 [SMILES: CCCN(CCC)C(=O)C1=Cc2ccc(C3=NCc4c(C)cccc4N3)cc2N=C(N)C1]

The title compound was prepared in analogy to Example 5 by using tent-butyl 2-amino-6-methylbenzylcarbamate instead of tent-butyl 2-amino-6-chlorobenzylcarbamate. Example 9 was obtained (29 mg) as a white solid. $^1$H NMR (400 MHz, MeOD) δ ppm=7.87-7.85 (m, 3H), 7.30-7.28 (m, 1H), 7.20-7.16 (m, 2H), 7.06-7.04 (s, 1H), 4.99 (s, 2H), 3.48 (br s, 4 H), 3.41 (s, 2H), 2.30 (s, 3 H), 1.75-1.69 (m., 4H), 0.99-0.93 (br s, 6H). MS: calc'd 430 (M+H)$^+$, measured 430 (M+H)$^+$.

Example 10

2-Amino-8-(5-fluoro-1,4-dihydroquinazolin-2-yl)-N,N-dipropyl-3H-1-benzazepine-4-carboxamide

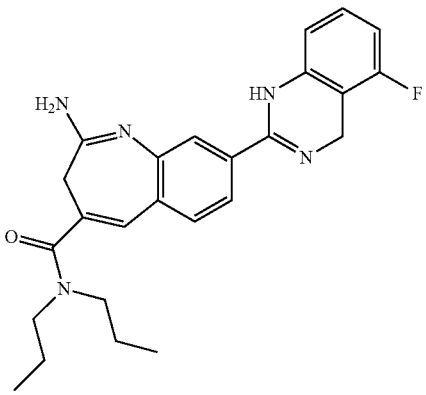 [SMILES: CCCN(CCC)C(=O)C1=Cc2ccc(C3=NCc4c(F)cccc4N3)cc2N=C(N)C1]

The title compound was prepared in analogy to Example 5 by using tent-butyl 2-amino-6-fluorobenzylcarbamate instead of tent-butyl 2-amino-6-chlorobenzylcarbamate. Example 10 was obtained (5 mg) as a white solid. $^1$H NMR (400 MHz, MeOD) δ ppm=7.87-7.83 (m, 3H), 7.46-7.40 (m, 1H), 7.13-7.06 (m, 3H), 5.03 (s, 2H), 3.46-3.31 (br s, 4 H), 3.30 (s, 2H), 1.72-1.67 (m., 4H), 0.98-0.97 (br s, 6H). MS: calc'd 434 (M+H)$^+$, measured 434 (M+H)$^+$.

Example 11

2-Amino-8-(6-methoxy-1,4-dihydroquinazolin-2-yl)-N,N-dipropyl-3H-1-benzazepine-4-carboxamide

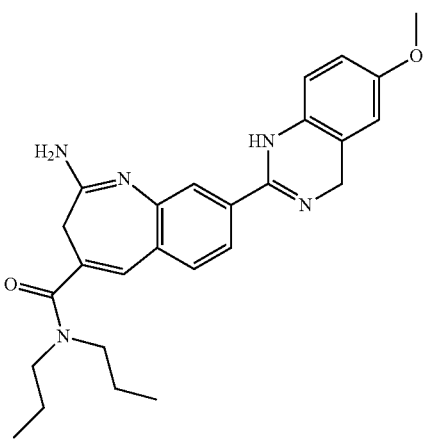 [SMILES: CCCN(CCC)C(=O)C1=Cc2ccc(C3=NCc4cc(OC)ccc4N3)cc2N=C(N)C1]

The title compound was prepared in analogy to Example 5 by using tent-butyl 2-amino-5-methoxybenzylcarbamate instead of tent-butyl 2-amino-6-chlorobenzylcarbamate. Example 11 was obtained (37 mg) as a white solid. $^1$H NMR (400 MHz, MeOD) δ ppm=7.85-7.84(m, 3H), 7.21-7.15 (m, 2H), 6.99-6.96 (m, 1H), 6.87-6.86 (m, 1H), 5.00 (s, 2H), 3.85 (s, 3H), 3.48 (br s, 4 H), 3.41 (s, 2H), 2.30 (s, 3 H), 1.74-1.69 (m., 4H), 1.00-0.93 (br s, 6H). MS: calc'd 446 (M+H)$^+$, measured 446 (M+H)$^+$.

The invention claimed is:

1. A benzazepine carboxamide compound of the formula I

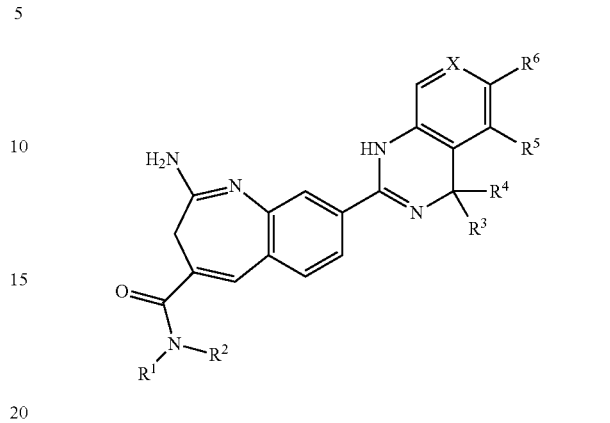

wherein
R$^1$ is C$_{3-7}$-alkyl;
R$^2$ is C$_{3-7}$-alkyl or C$_{3-7}$-cycloalkyl-C$_{1-7}$-alkyl;
R$^3$ is hydrogen or C$_{1-7}$-alkyl;
R$^4$ is hydrogen or C$_{1-7}$-alkyl;
R$^5$ is selected from the group consisting of hydrogen, halogen, C$_{1-7}$-alkyl and C$_{1-7}$-alkoxy;
R$^6$ is selected from the group consisting of hydrogen, halogen, C$_{1-7}$-alkyl and C$_{1-7}$-alkoxy;
X is N or CR$^7$, wherein R$^7$ is selected from the group consisting of hydrogen, halogen, C$_{1-7}$-alkyl and C$_{1-7}$-alkoxy;
or a pharmaceutically acceptable salt thereof.

2. The compound of claim 1, wherein R$^1$ is n-propyl.

3. The compound of claim 1, wherein R$^2$ is selected from the group consisting of n-propyl, isobutyl and cyclopropylmethyl.

4. The compound of claim 1, wherein R$^1$ and R$^2$ are n-propyl.

5. The compound of claim 1, wherein R$^3$ and R$^4$ are hydrogen.

6. The compound of claim 1, wherein R$^3$ and R$^4$ are methyl.

7. The compound of claim 1, wherein X is CR$^7$ and R$^7$ is selected from the group consisting of hydrogen, halogen, C$_{1-7}$-alkyl and C$_{1-7}$-alkoxy.

8. The compound of claim 7, wherein R$^7$ is hydrogen or halogen.

9. The compound of claim 1, wherein X is N.

10. The compound of claim 1, wherein R$^5$ is selected from the group consisting of hydrogen, halogen and C$_{1-7}$-alkyl.

11. The compound of claim 1, wherein R$^6$ is selected from the group consisting of hydrogen, halogen and C$_{1-7}$-alkoxy.

12. The compound of formula I according to claim 1, selected from:
2-amino-8-(1,4-dihydroquinazolin-2-yl)-N,N-dipropyl-3H-1-benzazepine-4-carboxamide;
2-amino-8-(1,4-dihydropyrido[3,4-d]pyrimidin-2-yl)-N,N-dipropyl-3H-1-benzazepine-4-carboxamide;
2-amino-N-(cyclopropylmethyl)-8-(1,4-dihydroquinazolin-2-yl)-N-propyl-3H-1-benzazepine-4-carboxamide;
2-amino-8-(1,4-dihydroquinazolin-2-yl)-N-isobutyl-N-propyl-3H-1-benzazepine-4-carboxamide;
2-amino-8-(5-chloro-1,4-dihydroquinazolin-2-yl)-N,N-dipropyl-3H-1-benzazepine-4-carboxamide;
2-amino-8-(7-chloro-1,4-dihydroquinazolin-2-yl)-N,N-dipropyl-3H-1-benzazepine-4-carboxamide;

2-amino-8-(4,4-dimethyl-1H-quinazolin-2-yl)-N,N-dipropyl-3H-1-benzazepine-4-carboxamide;

2-amino-8-(6-chloro-1,4-dihydroquinazolin-2-yl)-N,N-dipropyl-3H-1-benzazepine-4-carboxamide;

2-amino-8-(5-methyl-1,4-dihydroquinazolin-2-yl)-N,N-dipropyl-3H-1-benzazepine-4-carboxamide;

2-amino-8-(5-fluoro-1,4-dihydroquinazolin-2-yl)-N,N-dipropyl-3H-1-benzazepine-4-carboxamide; or 2-amino-8-(6-methoxy-1,4-dihydroquinazolin-2-yl)-N,N-dipropyl-3H-1-benzazepine-4-carboxamide, or a pharmaceutically acceptable salt thereof.

13. A pharmaceutical composition comprising a compound of formula I, or a pharmaceutically acceptable salt thereof, according to claim 1 and a pharmaceutically acceptable carrier and/or adjuvant.

14. A process for the manufacture of a compound of formula I of claim 1, or a pharmaceutically acceptable salt thereof, which process comprises:

a) coupling a compound of the formula II

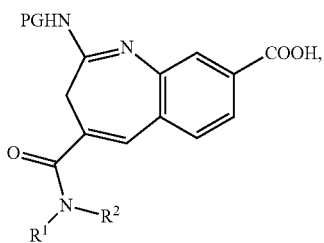

wherein $R^1$ and $R^2$ are as defined in claim 1 and PG is a protecting group, with a compound of the formula III

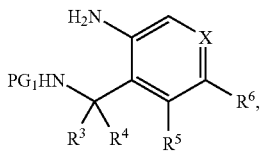

wherein X and $R^3$, $R^4$, $R^5$ and $R^6$ are as defined in claim 1 and $PG_1$ is a protecting group, under basic conditions in the presence of a coupling agent and removing the protecting groups PG and $PG_1$ under acidic conditions to obtain a compound of the formula I

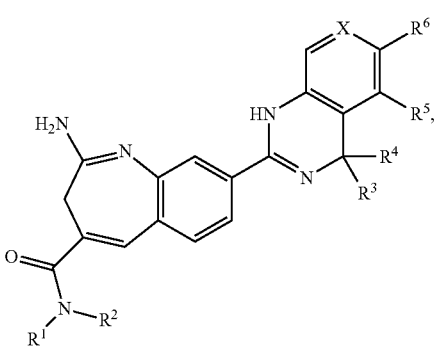

wherein X and $R^1$ to $R^6$ are as defined in claim 1, and, if desired, converting the compound obtained into a pharmaceutically acceptable salt.

* * * * *